United States Patent [19]
Adamany et al.

[11] Patent Number: 5,895,671
[45] Date of Patent: Apr. 20, 1999

[54] CHEESE CULTURE MEDIUM AND METHOD FOR PREPARING NO FAT AND LOW FAT CHEESE PRODUCTS

[75] Inventors: Anthony M. Adamany, Rockford; Thomas M. Henry, McHenry, both of Ill.; Deborah P. Moore; Craig S. Filkouski, both of Oconomowoc, Wis.

[73] Assignee: Conagra, Inc., Omaha, Nebr.

[21] Appl. No.: 08/664,435

[22] Filed: Jun. 18, 1996

Related U.S. Application Data

[60] Provisional application No. 60/016,709, May 2, 1996.

[51] Int. Cl.$^6$ .............. A23C 9/12; A23C 9/127; A23C 9/137; A23C 19/05
[52] U.S. Cl. .............. 426/36; 426/34; 426/39; 426/43; 426/491; 426/582
[58] Field of Search .............. 426/34, 36, 39, 426/42, 491, 582; 435/243, 252.1, 252.9, 253.3, 253.4, 253.6

[56] References Cited

U.S. PATENT DOCUMENTS

| | | | |
|---|---|---|---|
| 3,780,182 | 12/1973 | Johnson et al. | 426/33 |
| 3,840,672 | 10/1974 | Kasik et al. | 426/43 |
| 3,873,729 | 3/1975 | Kubota et al. | 426/40 |
| 3,882,250 | 5/1975 | Loter et al. | 426/39 |
| 3,922,376 | 11/1975 | Strinning et al. | 426/603 |
| 3,929,892 | 12/1975 | Hynes et al. | 426/582 |
| 3,953,610 | 4/1976 | Little et al. | 426/39 |
| 3,961,077 | 6/1976 | Kielsmeier | 426/36 |
| 3,969,534 | 7/1976 | Pavey et al. | 426/34 |
| 3,975,544 | 8/1976 | Kosikoski et al. | 426/35 |
| 4,000,332 | 12/1976 | Strinning et al. | 426/603 |
| 4,066,800 | 1/1978 | Rosenau et al. | 426/582 |
| 4,085,228 | 4/1978 | Reinbold et al. | 426/36 |
| 4,133,895 | 1/1979 | Kosikowski et al. | 426/33 |
| 4,169,160 | 9/1979 | Wingerd et al. | 426/40 |
| 4,169,854 | 10/1979 | Igoe et al. | 426/583 |
| 4,177,293 | 12/1979 | Forman et al. | 426/43 |
| 4,244,983 | 1/1981 | Baker et al. | 426/582 |
| 4,277,503 | 7/1981 | Bily et al. | 416/40 |
| 4,288,459 | 9/1981 | Baker et al. | 426/43 |
| 4,318,928 | 3/1982 | Sing et al. | 426/38 |
| 4,362,749 | 12/1982 | Sozzi et al. | 426/36 |
| 4,374,152 | 2/1983 | Loter et al. | 426/39 |
| 4,379,175 | 4/1983 | Baker et al. | 426/582 |
| 4,410,549 | 10/1983 | Baker et al. | 426/43 |
| 4,416,905 | 11/1983 | Lundstedt et al. | 426/34 |
| 4,434,184 | 2/1984 | Kharrazi et al. | 426/40 |
| 4,459,313 | 7/1984 | Swanson et al. | 426/39 |
| 4,476,143 | 10/1984 | Czulak et al. | 426/40 |
| 4,534,982 | 8/1985 | Yoshida et al. | 426/36 |
| 4,547,385 | 10/1985 | Lindstam et al. | 426/570 |
| 4,568,555 | 2/1986 | Spanier et al. | 426/582 |
| 4,631,196 | 12/1986 | Zeller et al. | 426/580 |
| 4,684,533 | 8/1987 | Kratochvil et al. | 426/575 |
| 4,689,234 | 8/1987 | Ernstrom et al. | 426/38 |
| 4,713,254 | 12/1987 | Childs et al. | 426/582 |
| 4,719,113 | 1/1988 | Kharazi et al. | 426/35 |
| 4,719,118 | 1/1988 | Thomas et al. | 426/580 |
| 4,724,152 | 2/1988 | Baker et al. | 426/335 |
| 4,732,769 | 3/1988 | Sozzi et al. | 426/240 |
| 4,749,584 | 6/1988 | Wirchansky et al. | 426/582 |
| 4,806,479 | 2/1989 | Kegel et al. | 435/244 |
| 4,837,035 | 6/1989 | Baker et al. | 426/43 |
| 4,837,036 | 6/1989 | Baker et al. | 426/43 |
| 4,851,243 | 7/1989 | Andersen et al. | 426/74 |
| 4,906,481 | 3/1990 | Bussiere et al. | 426/39 |
| 4,917,905 | 4/1990 | Guy et al. | 426/39 |
| 4,919,944 | 4/1990 | Bussiere et al. | 426/39 |
| 5,011,701 | 4/1991 | Baer et al. | 426/573 |
| 5,037,659 | 8/1991 | Trecker et al. | 426/40 |
| 5,215,778 | 6/1993 | Davidson et al. | 426/582 |
| 5,395,630 | 3/1995 | Gamey | 426/39 |

FOREIGN PATENT DOCUMENTS

| 834092 | 2/1970 | Canada. |
| 1248407 | 1/1989 | Canada. |
| 1374094 | 9/1971 | United Kingdom. |
| 2106366 | 9/1982 | United Kingdom. |
| 2214776 | 8/1988 | United Kingdom. |

OTHER PUBLICATIONS

Effect of Enzyme Treatment and Ultrafiltration on the Qualoty of Lowfat Cheddar, J.U. McGregor and C.H. White, Department of Dairy Science, 1990.

*Primary Examiner*—Michael P. Woodward
*Assistant Examiner*—Mary K. Zeman
*Attorney, Agent, or Firm*—Pretty, Schroeder & Poplawski

[57] ABSTRACT

Disclosed is a method for preparing a no fat or low fat cheese product from a culture medium prepared by combining from about 50 to about 94 wt. % whole milk, from about 0 to about 45 wt. % water, and from about 0.2 to about 1 wt. % of at least one food grade, polyanionic gum. The culture medium is inoculated with at least one lactic acid- or heteroacid producing bacterium to form a cultured mixture. The cultured mixture is then combined in a vat with skim or low fat milk to form a cultured milk. The cultured milk is ripened, sufficient rennet added to form a coagulum, the coagulum cut to form curd in a whey solution, and the curd cooked while in the whey solution. The cooked curd is transferred to a means for draining the whey solution where the whey is separated from the curd and the curd salted. After salting, the curd is further processed to produce a no fat or low fat cheese.

9 Claims, No Drawings

5,895,671

1

CHEESE CULTURE MEDIUM AND METHOD FOR PREPARING NO FAT AND LOW FAT CHEESE PRODUCTS

PRIORITY

This application claims priority based on Ser. No. 60/016,709 filed May 2, 1996.

BACKGROUND OF THE INVENTION

1. Field of the Invention

This invention relates to the chemical arts. In particular, it relates to a culture medium and a cultured milk used to make no fat or low fat cheese products and to a method for making such cheese products.

2. Discussion of the Related Art

In recent years, for health as well as cosmetic reasons, there has developed an increasing concern with diet which has focused on reduced fat consumption. Low fat foods which look and taste like their higher fat counterparts have been eagerly sought by the public. To this end, food researchers have concentrated on developing food products which are nutritious and palatable, but which contain substantially reduced levels of fat. This is particularly true in the dairy industry where such reduced fat products as skim milk and yogurt have been successfully marketed. However, the successes in these areas have not carried over to methods for preparing no fat or low fat cheeses having high consumer acceptance.

Attempts have been made to use skim or low fat milk in conventional cheese making processes, to produce no fat or low fat cheeses. Unfortunately, the body, texture and flavor of the resulting no fat or low fat cheese products have not been entirely satisfactory for ordinary consumer use. The cheeses tend to be extremely hard, leathery and tough, and are often almost completely devoid of flavor. Therefore, it is a desideratum for a process which results in the preparation of no fat or low fat cheese products having similar body, texture and flavor when compared to their full fat counterparts.

Typically, in the manufacture of no fat or low fat cheese, raw or pasteurized skim or low fat milk is placed in a vat and heated to an appropriate temperature. Bacteria, such as *S. cremoris, S. lactis, S. citrovorous, S. thermophillus, L. bulgaricus, L. casei and L. heleveticus,* are approved lactic acid- and hetero-acid-producing cultures that when added to the milk begin to produce lactic acid and other products, such as fatty acids, butyrates and octanoates, which effect the body, texture and flavor of the final cheese product. To aid in their production, the acid bacteria are often combined with a culture medium before addition to the milk.

After addition of the bacteria, the milk is allowed to ripen until a desired degree of acid has been produced. The milk at this stage is known as cultured milk. Rennet is added to the cultured milk to form a coagulum. When the coagulum has reached a desired degree of finnness, it is cut to form curd in a whey solution. The vat is then heated to between about 95° F. and 120° F. and held at a temperature in this range for a period of time sufficient to cook the curd, causing the curd to continue firming and the bacteria to continue producing lactic acid and other products which effect the body, texture and flavor of the final cheese product. The whey solution is then drained, leaving a firm, resilient curd. The disposal of whey can be a problem and it is desirable to be able to recycle the whey to the greatest possible extent. Consequently, it is also a desideratum to maximize the

2 amount of recyclable whey that can be recovered from a no fat or low fat cheese making process.

After the vat is drained of the whey solution, the curd is salted. In certain conventional processes, salting cannot occur until after bacteria have produced sufficient acid to cause the curd to have a pH of less than 5.5. The addition of salt has the affect, inter alia, of significantly decreasing the bacterial activity, thereby lessening production of additional lactic acid and other products. After salting, the cheese is typically further processed, such as by aging which allows additional development of lactic acid and other byproducts effecting the final body, texture and flavor of the desired cheese product. Because the salting step slows down the production of lactic acid and other products, aging can be a time-consuming process requiring from several weeks to several years.

It can be appreciated from the above description that the cheese making process is time-consuming, particularly because of the time required for the pH and flavor of the curd to develop before salting and because of the time required to ripen the cheese after it has been salted. Therefore, it is also a desideratum to minimize the time required to manufacture no fat or low fat cheese with desirable attributes and thereby increase the efficiency of the cheese making process.

Accordingly, there has existed a definite need for an improved method for preparing no fat and low fat cheese products having a more similar body, texture and flavor when compared to their full fat counterparts. There has existed a still further need for an improved method for preparing no fat or low fat cheese products minimizing the time required to produce a final cheese product, while maximizing the amount of recyclable whey. The present invention satisfies these and other needs and provides further related advantages.

SUMMARY OF THE INVENTION

In accordance with the invention, there has been found a cheese culture medium and a cultured milk that enhance the development of lactic acid, hetero-acids and other products of the bacteria used in cheese making processes. Because of the enhanced development, it is possible to produce reduced fat cheese products having a more similar body, texture and flavor when compared to their full fat counterparts. Further, because of the enhanced development, it is possible to shorten or eliminate various steps required throughout conventional cheese making processes for the production of lactic acid, hetero-acids and other products.

The cheese culture medium contains from about 50 to about 94 wt. %, preferably about 55 to about 65 wt. %, whole milk, from about 0 to about 45 wt. %, preferably about 35 to about 45 wt. %, water, and from about 0.2 to about 1 wt. %, preferably from about 0.3 to about 0.5 wt. %, of at least one food grade, polyanionic gum, where the weight percents are based on the total weight of the culture medium. Representative anionic gums include agar, xanthan, alginate, guar, carrageenan, cellulose gels, such as carboxymethyl cellulose, and the like.

In preferred embodiments, the culture medium also contains from about 1 to about 4 wt. % of a nonionic thickener, such as a modified food starch, from about 0.1 to about 1 wt. % of at least one emulsifying salt, such as sodium citrate, sodium phosphate, dipotassium phosphate or combinations thereof, and from about 1 to about 5 wt. % of at least one nutrient source, such as yeast extract, yeast autolysate, solubilized yeast, food yeast, magnesium sulfate, enzyme hydrolyzed casein, amino acids, proteins, nonfat dry milk.

sweet whey powder, simple sugars, such as lactose, and mixtures thereof, where the weight percents are based on the total weight of the culture medium. Additional ingredients that can be included in the culture medium include flavorings, fat mimetics and fat emulsifiers, to decrease the size of the fat droplets and disperse the fat droplets evenly, and opacifying agents, such as titanium dioxide.

In accordance with the invention, no fat or low fat cheeses are produced by pasteurizing the culture medium, and then cooling the medium to a temperature suitable for growth of lactic acid-, hetero-acid, or flavor producing bacteria. The culture medium is then inoculated with lactic acid-, hetero-acid or flavor producing bacteria and the mixture developed to form a cultured mixture. Cultured milk is then made by adding, in a vat, from about 3 to about 8 wt. % of the cultured mixture, based on the weight of the cultured milk, to skim or low fat milk. In some embodiments, flavor promoter, coloring, and/or calcium chloride are added along with the cultured mixture and the skim or low fat milk. The cultured milk is allowed to ripen and sufficient rennet is added to the ripened milk to form a coagulum. The coagulum is then cut to form curd in a whey solution and the curd cooked, before draining the whey solution and salting the curd. In some embodiments, at least about 50 wt. % of the whey solution is predrawn based on the total weight of whey solution in the vat, before the curd is transferred from the vat to means for draining the whey solution, and the remainder of the whey solution drained away. And in some embodiments, salting begins when the pH of the curd is 5.6 or greater. After salting, processing is completed to produce a reduced fat cheese having a body, texture and flavor more similar when compared to its full fat counterpart.

DESCRIPTION OF THE PREFERRED EMBODIMENTS

To exemplify the process in accordance with the invention, the following description may concentrate primarily on a method for preparing reduced fat mozzarella cheese using, for example, a drain table to finally separate the curd from the whey solution. It should be readily apparent to the skilled artisan that the description, with little modification, might also apply to preparing other reduced fat cheeses. For example, low fat or no fat American, cheddar, colby, provolone, and the like can all be prepared in accordance with the inventive method. Further, there can be modifications in the equipment used. For example, a continuous, perforated belt can be used instead of the drain table to complete separation of the curd from the whey solution.

The culture medium in accordance with the invention contains from about 50 to about 94 wt. %, preferably from about 55 to about 65 wt. %, whole milk, based on the weight of the culture medium. The term whole milk, as used herein, means milk having a butterfat content of from about 3.0 to about 4.5% butterfat, preferably about 3.5 to about 4% butterfat, based on the weight of the whole milk. The term whole milk also includes combinations of various butterfat content milks and equivalent compositions formed by suitable admixtures of milk solids and water having comparable butterfat contents. The butterfat content of the milk is important to the practice of the invention. If the milk contains too little butterfat, use of the resulting culture medium will not produce no fat or low fat cheeses having the same desirable body, texture and flavor, as cheeses prepared with the culture medium in accordance with the invention. On the other hand, if the butterfat content of the milk is too great, there is an unnecessary increase in the fat content of the cheese product, without any attendant improvement in its body, texture or flavor.

The culture medium also contains from about 0 to about 45 wt. %, preferably from about 35 to about 45 wt. %, water, based on the weight of the culture medium. The amount of water to be used in a particular application is chosen to adjust the viscosity of the culture medium and, ultimately, the viscosity of the culture mixture.

Another ingredient contained in the culture medium is a food grade, polyanionic gum stabilizer. Representative anionic gums include agar, xanthan, alginate, guar, carrageenan, cellulose gels, such as carboxymethyl cellulose, and the like, as well as mixtures thereof. The polyanionic gum stabilizer is added in an amount sufficient to help stabilize the solids in the subsequently produced culture mixture. The stabilizer also helps in preventing the resulting curd from having an undesirable rubbery texture. The polyanionic gum stabilizer is typically added to the culture in an amount from about 0.2 to about 1.0 wt. %, preferably from about 0.3, to about 0.5 wt. %, based on the weight of the culture medium. Without wishing to be bound by a theory of the invention, it is believed that by adding the stabilizer to whole milk certain stabilizer/fat culture interactions occur which enhance the body, texture and flavor of the subsequently formed cheese. Such interactions are less likely to occur, if they occur at all, when the stabilizer is directly added to skim or low fat milk.

In preferred embodiments, the culture medium also contains from about 1 to about 4, preferably from about 2 to about 3 wt. %, of a nonionic thickener, such as a modified food starch, based on the weight of the culture medium. The nonionic thickener is added in an amount sufficient to aid in imparting a softer texture to the resulting curd. The nonionic thickener also develops a soft gel to the culture mixture that prevents solids from separating after the mixture has been added to the mixing vessel.

The culture medium can also contain from about 0.1 to about 1.0 wt. %, preferably from about 0.25 to about 0.5 wt. %, of an emulsifying salt, based on the weight of the culture medium. Emulsifing salts are added in an amount sufficient to buffer the culture media and sequester calcium. Representative salts include monosodium phosphate, disodium phosphate, dipotassium phosphate, trisodium phosphate, sodium metaphosphate (sodium hexametaphosphate), sodium acid phosphate, tetrasodium pyrophosphate, sodium aluminum phosphate, sodium citrate, potassium citrate, calcium citrate, sodium tartrate, sodium potassium tartrate and mixtures thereof. Sodium citrate, sodium phosphate or dipotassium phosphate are preferred. An additional advantage of phosphate-containing emulsifiers, is that the phosphate is a nutrient source for the acid-producing bacteria and of dipotassium phosphate is that potassium is also a nutrient source for the acid-producing bacteria.

Other nutrient sources can be added to the culture medium, typically in an amount from about 1 to about 5 wt. %, based on the weight of the culture medium. An amount from about 2 to about 3 wt. % is preferred. Suitable nutrient sources include nitrogen sources, such as yeast extract, yeast autolysate, solubilized yeast, food yeast, enzyme hydrolyzed casein, amino acids, and proteins, as well as other nutrients, including nonfat dry milk, sweet whey powder, simple sugars, such as lactose, sodium phosphates and magnesium sulphate.

It is also possible to add flavorings, typically in an amount from about 0.1 to about 1.5 wt. %, based on the weight of the culture medium. Flavorings containing little or no fat are preferred, so that they will not add significantly to the fat content of the final cheese product. Representative no fat or low fat flavorings include buttermilk solids and natural and artificial butter and dairy flavor components. Additional ingredients that can be included in the culture medium include fat mimetics, such as propylene glycol monoester (which also may help in stabilizing and evenly dispersing the fat) and opacifying agents, such as titanium dioxide.

The culture medium is made by mixing the ingredients to form a slurry. The slurry is pasteurized, for example, by heating to 190° F. for thirty seconds. The culture medium is then cooled to a temperature of from about 75° F. to about 108° F., preferably about 90° F. to about 96° F., before inoculating with acid-producing bacteria.

Lactic acid-, hetero-acid, and flavor producing bacteria for use in cheese making are well known in the art and the choice of a particular bacterium or combination of bacteria will depend on the type of cheese to be produced. Representative bacteria suitable for practice of the invention include, without limitation, *S. cremoris, S. lactis, S. citrovorous, S. paracitrovorus, S. thermophillus, S. durans, S. diacetilactis, S. faecalis, L. acidophilus, L. bulgaricus, L. brevis, L. casei, L. delbruekii, L. fermenti, L. heleveticus, L. lactis, L. plantarum, L. thermophillus, leuconsostoc eitrovorum, leuconsostoc mesenteroides, Bacteriumlinesn, Micrococcus caseolyticus, Pediococcus cerevisiae, Pseudomonas fraga* and *propionibacterium species*, such as *Propionibacterium shermanii*. In the manufacture of no fat or low fat mozzarella cheese, *L. casei* or a combination of *S. thermophillus* and *L. bulgaricus* are preferred.

While maintaining the elevated temperature, the mixture is developed for several hours, until a pH from about 4.8 to about 4.6, preferably about 4.7 is attained. The resulting cultured mixture is cooled, while continuously stirring, to a temperature of from about 40° F. to about 48° F., preferably about 45° F., and a pH of from about 4.7 to about 4.4, preferably about 4.6.

In contrast to the whole milk used to form the culture medium, in the making of the cultured milk, the cultured mixture is added to skim milk (milk having a butterfat content less than 0.5%) or low fat milk (milk having a butterfat content less than 2.0%). As used herein, skim and low fat milks include equivalent compositions formed by suitable admixtures of milk solids and water. The skim milk can be raw milk, but is preferably pasteurized and fortified to a desired vat protein level. Typically, cultured milk is formed by adding from about 3 to about 8 wt. % cultured mixture, preferably about 5 to about 7 wt. % cultured mixture, based on the weight of the cultured milk, to skim or low fat milk having a temperature of about from about 75° F. to about 108° F., preferably about 96° F. It is an advantage of the process in accordance with the invention that the skim milk or low fat milk can have any butterfat level below the final desired butterfat level and then the final butterfat level simply and reliably achieved by adding the requisite amount of the whole milk-based cultured mixture. The final butterfat level in the vat is normally in the range of from about 0.1 to about 0.5%, preferably from about 0.2 to about 0.3%, based on the weight of the cultured milk, depending on the desired fat content of the final cheese product.

Other ingredients can be added along with the cultured mixture and whole milk into a stainless steel vat or similar mixing vessel. For example, the cultured milk mixture can include from about 0.005 to about 0.02 wt. % calcium chloride, based on the weight of the cultured milk. The calcium chloride can be added in dry form, but it is preferably added in the form of an aqueous solution. The period of ripening is affected by the presence of calcium chloride; the absence of calcium prolonging the ripening period. The added calcium chloride also serves to replace natural calcium chloride lost from the milk. The cultured milk can also include such conventional ingredients as flavor promoters and colorings. Ingredients, such as flavorings and opacifying agents, if not added to the cultured mixture, can also be added or they can be added in addition to the amounts included in the cultured mixture.

The cultured milk is then ripened by maintaining the temperature between about 75° F. and about 98° F., preferably between about 95 to about 98° F., with stirring, for about 15 to about 40 minutes, preferably about 35 minutes. The pH of the ripened milk at the end of this period is generally from about 6.35 to about 6.65.

A clotting enzyme is mixed into the ripened milk to cause the milk to coagulate. Suitable clotting enzymes include rennet, rennin, a diluted rennin extract, a pepsin-rennin mixture, a vegetable-derived enzyme clotting agent or the like. Rennet is preferred. Other enzymes such as pepsin and papain may be used alone or in combination with the rennet or rennin. After addition of the clotting enzyme, the mixture is allowed to set without stirring for about 20 to 40 minutes, typically about 30 minutes, to form a firm, set coagulum.

Once set, the coagulum is cut. It is first cut mechanically using vertical and horizontal curd knives. After removal of the curd knives, it is manually cross-cut with a vertical knife. Cutting of the stable coagulum causes whey syneresis and leads to a heterogeneous mixture of curd in a whey solution.

The curd is then cooked, while in the whey solution. For no fat or low fat mozzarella cheese, the temperature of the curd in the whey solution is gradually raised to from about 96° F. to about 118° F., preferably to 106° F., within a period of from about 20 about 40 minutes, preferably, from about 30 to about 35 minutes.

Shortly after cooking and before the curd is transferred to a draining table, up to about 50%, typically up to about 35%, of the whey solution is predrawn from the curd. This step has the advantage of producing unadulterated whey, especially suitable for recycling. The curd and the remainder of the whey solution are then transferred to a draining table. As the mixture is stirred the remaining whey solution is drained from the curd and the curd salted.

In certain conventional processes, salting does not occur until after bacteria have produced sufficient lactic acid to cause the curd to have a pH of less than 5.5. It is an advantage of the inventive process that salting can begin, without waiting for the pH to drop to less than 5.5. For example, in the preparation of reduced fat cheddar cheeses, the curd can be salted when it has a pH of 5.6 or greater.

After salting are a number of steps particularly suited for the preparation of mozzarella cheese. The salted curd is conveyed to a mozzarella-type, steam injected cooker and heated to form a homogeneous, thermoplastic mass with an internal temperature of about 140° F. The cheese mass is then sent through a molder to make loaf- or ball-shaped forms.

The formed cheese is chilled by conveying through a chill tank. The cheese is then removed from its form and further chilled and salted by passing through a brine tank. Lastly, the cheese is drained and then packaged.

Alternatively, the thermoplastic mass can be conveyed through a separate molder followed by a string-forming extruder. The resulting strings are cut into pieces and the pieces are then passed through a brine tank, drained, and packaged.

In contrast, if the desired no fat or low fat cheese is a cheddar cheese, the salted cheese curd is transferred directly to forms, hoops, or barrels. The cheese is then pressed to expel entrapped whey and allowed to knit. After knitting the cheese is aged.

The following examples are included to further illustrate the invention. They are not a limitation thereon. All percentages are based on weight unless otherwise clearly indicated.

EXAMPLE 1

A no fat mozzarella cheese is prepared by the following method.

Preparation of Culture Medium

The following ingredients are mixed to form a slurry: 58.7% whole milk, 35.8% water, 4.3% Bunge Stabilset, 0.2% dipotassium phosphate, 1.0% Pfizer Autostat, and 0.2% natural flavor. Bunge Stabilset (available from Dari-Tech Industries, Atlanta Ga.) is an admixture of agar, xanthan gum, cellulose gel, locust bean gum, modified food starch, sodium phosphate, sodium citrate, propylene glycol monoester, and titanium dioxide. Pfizer Autostat is a nutrient source (available from Pfizer, Milwaukee, Wis.) containing a soluble growth factor from $S.$ $cerevisiae$, lactose, disodium phosphate and magnesium sulphate. The resulting slurry is pasteurized to 190° F. for 30 seconds and then cooled to 106° F.

Preparation of Cultured Mixture

The slurry is inoculated with 1.0% of a mixture of $S.$ $thermophillus$ and $L.$ $bulgaricus$ bacteria based on the weight of the cultured mixture. The bacteria are allowed to grow for several hours until the pH reaches 4.8. The cultured mixture is then continuously stirred, while cooling to 45° F. At this point a final pH of 4.7 is attained.

Preparation of Skim Milk

Whole milk is standardized to 3.6% vat protein by fortifying with nonfat dry milk. The fortified milk is then skimmed to the lowest possible fat level (0.05–0.07%) in a milk separator. The separated milk is pasteurized to 164° F. for 17 seconds and then passed through a vacuutherm to cool the milk to 96° F.

Preparation of Mozzarella Curd

Fifteen hundred pounds of the cultured mixture is added to a stainless steel vat as the vat receives about 31,000 pounds of skim milk at a rate of about 51,000 pounds per hour. The following ingredients are also added at this time: two cans (360 mls each) of flavor promoter, $L.$ $casei$ (LF304, available from Cultor Foods, Milwaukee, Wis.), 0.75 oz. of Annatto cheese color and 11.89 pounds of 30% aqueous calcium chloride (Cal Sol, available from systems Bio Industries, Waukesha, Wis.). The combined ingredients are stirred and allowed to ripen for about 35 minutes from the time the cultured mixture is added, achieving a pH of about 6.6 and a titratable acidity of about 0.2%.

After ripening, 30 oz. of double strength rennet (Maxiren, available from Gist Brocades, Menomonee Falls, Wis.), diluted with 10 times the volume of water, is poured into the ripened blend, along the length of the vat. The blend is mixed with an agitator until the rennet is evenly distributed in the milk and then allowed to set without stirring for about 30 minutes.

Once the blend becomes a firm, set coagulum, it is cut mechanically using an ½" vertical and a ⅛" horizontal set of curd knives. Formation of a curd in a whey solution begins as the stable coagulum is cut. The curd knives are carefully removed and the curd is cross-cut manually with an ½" vertical knife.

The resulting mixture of curd in a whey solution is stirred for about 10 minutes and then, with continued, continuous stirring is cooked by gradually increasing the temperature from 92°–104° F. within a period of about 35 minutes.

Ten minutes after cooking is completed, about one-third of the whey solution is drawn from the vat. The residual whey solution and the curd are then transferred by gravity to a draining table and the remaining whey solution immediately, completely drained. The pH at this point is about 6.15 and the titratable acidity about 0.17–0.19%. The drained curd is stirred until a pH of about 5.35 and a titratable acidity of about 0.45–0.50% is reached. Then 50 pounds of salt is evenly distributed across the curd in two application of 25 pounds and the stirring continued for 10 minutes.

Preparation of Mozzarella

The curd is conveyed to a mozzarella-type, steam-injected cooker containing water heated to 185–190° F., where the curd forms a homogeneous, thermoplastic mass with an internal temperature of about 138° F. The cheese mass is then sent through a molder into loaf-shaped forms.

The formed cheese is chilled by conveying through a chill tank. The cheese is then removed from its form and further chilled and salted by passing through a brine tank. Lastly, the cheese is drained and then packaged. The no fat mozzarella cheese produced in accordance with this example has a body, texture and flavor that compares very favorably with its full fat counterpart.

EXAMPLE 2

A no fat cheese is prepared by the following method.

Preparation of Cultured Medium

Culture Medium A

The following ingredients are mixed to form a slurry: 89% water, 10% sweet whey powder, and 1% Pfizer Autostat. The resulting slurry is pasteurized to 185° F. for 30 minutes and then cooled to 106° F.

Culture Medium B

The following ingredients are mixed to form a slurry: 59% whole milk, 35.75% water, 4% Bunge Stabilset, 1% dipotassium phosphate, and 0.25% Pfizer Autostat. The resulting slurry is pasteurized to 190° F. and then cooled to 90° F.

Preparation of Cultured Mixture

Cultured Mixture A

Culture medium A is inoculated with 1.00% of a mixture of $S.$ $thermophillus$ and $L.$ $bulgaricus$ bacteria. The bacteria are allowed to grow for several hours until the pH reaches 4.60. The cultured mixture is then continuously stirred, while cooling to 45° F. At this point a pH of 4.50 is attained.

Cultured Mixture B

Culture medium B is inoculated with $L.$ $casei$ (PLCI, available from Cultor Foods, Milwaukee, Wis.). The bacteria are allowed to grow for four hours and then cooled with stirring to a temperature of 45° F. At this point, the acid-producing bacteria has acclimated from the frozen state and multiplied several generations.

Preparation of Curd

Three hundred pounds of cultured mixture A, 2300 pounds of cultured mixture B, and 50 ounces Cal Sol, 30% calcium chloride, are added to a double 0 vat as the vat receives about 45,000 pounds of skim milk prepared in accordance with Example 1. The combined ingredients are stirred and allowed to ripen for about 40 minutes from the time the cultured mixture is added, achieving a pH of about 6.40 and a titratable acidity of about 0.21%.

After ripening, 26 oz. of Maxiren, double strength rennet, diluted with 10 times the volume of water is poured into the ripened blend, along the length of the vat. The blend is mixed with an agitator set at 5½ rpms, for 2 minutes, then allowed to set without stirring for thirty minutes. Formation of a curd in a whey solution begins as the stable coagulum is cut as explained in Example 1.

The resulting mixture of curd in a whey solution is stirred for about 5 minutes, at 6 ½ rpms and then, with continued, continuous stirring is cooked by gradually increasing the temperature from 96° F. to 100° F. with a gradual increase in agitator speed to 8½ rpms. Stirring then continues as the agitator speed is brought to 10½ rpms and the temperature is brought to 110° F.

After cooking is completed, the stirring is continued, until a pH of 6.10 is achieved. The curd in the whey solution is then pumped by a positive pump to an inclined draining belt where all the whey solution is immediately drained. The curd, at this point, has a pH of 6.00. The curd is then piled onto a continuously moving belt for 30 minutes and the pH developed to below 5.50. After 25 minutes on the belt, the curd is salted.

Preparation of Cheese

The salted curd is cut and transferred to a cooker/mixer where it is cooked in 180 F. water to produce a molten cheese having a temperature of 135–140° F. The resulting molten cheese is poured into an extruder and loaves are formed.

The loaves are cooled in chilled water for 30 minutes and then transferred for further cooling and salting in a 90% salinity brine for over 3½ hours. The product is then washed, drained, and packaged. The no fat cheese produced in accordance with this example has a body, texture, and flavor that compares very favorably with full fat cheese.

I claim:

1. A method for preparing a no fat cheese product comprising the steps of:
   preparing a culture medium by combining:
      from about 50 to about 94 wt. % whole milk, based on the weight of the culture medium,
      from about 0 to about 45 wt. % water, based on the weight of the culture medium, and
      from about 0.2 to about 1 wt. % of at least one food grade, polyanionic gum selected from the group comprising agar, xanthan, alginate, guar, carrageenan, and cellulose gels, based on the weight of the culture medium, to form a culture medium;
   pasteurizing the culture medium;
   cooling the pasteurized culture medium to a temperature suitable for the growth of acid-producing bacteria;
   inoculating the culture medium with at least one acid-producing bacteria selected from the group consisting of S. cremoris, S. lactis, S. citrovorous, S. paracitrovorus, S. thermophillus, S. durans, S. diacetilactis, S. faecalis, L. acidophilus, L. bulgaricus, L. brevis, L. casei, L. delbruekii, L. fermenti, L. heleveticus, L. lactis, L. plantarum, L. thermophillus, Leuconsostoc eitrovorum, Leuconsostoc mesenteroides, Bacteriumlinesn, Micrococcus caseolyticus, Pediococcus cerevisiae, Pseudomonas fraga and propionibacterium species;
   developing and then cooling the thus formed mixture, to form a cultured mixture having a pH of from about 4.8 to about 4.6;
   forming cultured milk by mixing in a vat from about 3 to about 8 wt. % milk, based on the weight of the cultured milk, cultured mixture with standardized and pasteurized skim milk, the cultured milk having a butterfat content of from about 0.1 to about 0.5%, based on the weight of the cultured milk;
   ripening the cultured milk;
   adding sufficient rennet to the ripened milk to form a coagulum;
   cutting the coagulum to form curd in a whey solution;
   cooking the curd while in the whey solution;
   transferring the curd in the whey solution to a means for draining the whey solution and then draining the whey solution from the curd;
   salting the curd; and
   further processing the salted curd to produce a no fat cheese having the body, texture, and flavor similar to its full fat counterpart.

2. The method in accordance with claim 1 further comprising adding to the culture medium from about 1 to about 4 wt. %, based on the weight of the culture medium, of a non-ionic thickener.

3. The method in accordance with claim 2 wherein the non ionic thickener is a modified food starch.

4. The method in accordance with claim 2 further comprising adding to the culture medium from about 0.1 to about 1 wt. %, based on the weight of the culture medium, of at least one emulsifying salt selected from the group consisting of monosodium phosphate, disodium phosphate, dipotassium phosphate, trisodium phosphate, sodium metaphosphate, sodium acid phosphate, tetrasodium pyrophosphate, sodium aluminum phosphate, sodium citrate, potassium citrate, calcium citrate, sodium tartrate, sodium potassium tartrate, and mixtures thereof.

5. The method in accordance with claim 4 wherein the emulsifying salt is selected from the group consisting of sodium citrate, sodium phosphate or dipotassium phosphate and mixtures thereof.

6. The method in accordance with claim 4 further comprising adding to the culture medium from about 1 to about 5 wt. %, based on the weight of the culture medium, of at least one nutrient source for the lactic acid-forming bacteria selected from the group consisting of yeast extract, yeast autolysate, solubilized yeast, food yeast, enzyme hydrolyzed casein, sodium phosphates, magnesium sulphate and mixtures thereof.

7. The method in accordance with claim 1 comprising predrawing up to about 50 wt. % of the whey solution from the vat, based on the total weight of the whey solution in the vat, after cooking and before transferring the whey solution to the means for draining whey solution.

8. A method in accordance with claim 1 wherein salting begins when the pH of the curd is 5.6 or greater.

9. A method for preparing a no fat cheese product comprising the steps of:
   preparing a culture medium by combining
      from about 55 to about 65 wt. % whole milk, based on the weight of the culture medium, the whole milk having a butterfat content of from about 3.0 to about 4.5 wt. %, based on the weight of the whole milk,
      from about 35 to about 45 wt. % water, based on the weight of the culture medium,
      from about 0.3 to about 0.5 wt. % of at least one food grade, polyanionic gum selected from the group comprising agar, xanthan, alginate, guar, carrageenan, and cellulose gels, based on the weight of the culture medium, to form a culture medium,
      from about 2 to about 3 wt. %, based on the weight of the culture medium, of a modified food starch, from about 0.25 to about 0.5 wt. %, based on the weight of the culture medium, of at least one emulsifying salt selected from sodium citrate, sodium phosphate, dipotassium phosphate or mixtures thereof, and from about 2 to about 3 wt. %, based on the weight of the culture medium, of at least one nutrient source for lactic acid-producing bacteria selected from yeast extract, yeast autolysate, solubilized yeast, food yeast, enzyme hydrolyzed casein, sodium phosphates, magnesium sulphate or mixtures thereof, pasteurizing the culture medium;

cooling the pasteurized culture medium to a temperature suitable for the growth of acid-producing bacteria;

inoculating the culture medium with at least one acid-producing bacteria selected from the group consisting of *S. cremoris, S. lactis, S. citrovorous, S. paracitrovorus, S. thermophillus, S. durans, S. diacetilactis, S. faecalis, L. acidophilus, L. bulgaricus, L. brevis, L. casei, L. delbruekii, L. fermenti, L. heleveticus, L. lactis, L. plantarum, L. thermophillus, Leuconsostoc eitrovorum, Leuconsostoc mesenteroides, Bacteriumlinesn, Micrococcus caseolyticus, Pediococcus cerevisiae, Pseudomonas fraga* and *propionibacterium* species;

developing and then cooling the thus formed mixture, to form a cultured mixture having a pH of from about 4.8 to about 4.6;

forming cultured milk by mixing in a vat from about 5 to about 7 wt. % milk, based on the weight of the cultured milk, with standardized and pasteurized skim milk, the cultured milk having a butterfat content of from about 0.2 to about 0.3%, based on the weight of the cultured milk;

ripening the cultured milk;

adding sufficient rennet to the ripened milk to form a coagulum;

cutting the coagulum to form curd in a whey solution;

cooking the curd while in the whey solution;

drawing up to about 35 wt. % of the whey solution from the vat, based on the total weight of the whey solution in the vat;

transferring the curd and the remaining whey solution to a means for draining the whey solution and then draining the remaining whey solution from the curd;

salting the curd, when the curd has a pH of 5.6 or greater; and futher processing the salted curd to produce a no fat cheese having the body, texture, and flavor similar to its full fat counterpart.

* * * * *